US011523618B2

(12) United States Patent
Hartwig et al.

(10) Patent No.: US 11,523,618 B2
(45) Date of Patent: Dec. 13, 2022

(54) X-RAY INSPECTION OF MEAT

(71) Applicant: Mettler-Toledo, LLC, Columbus, OH (US)

(72) Inventors: Norbert Hartwig, Waldems-Esch (DE); Michael A. Evans, Land O Lakes, FL (US); Kristofer Loper, Lutz, FL (US); Christopher Sisemore, Land O Lakes, FL (US)

(73) Assignee: METTLER-TOLEDO, LLC, Columbus, OH (US)

( * ) Notice: Subject to any disclaimer, the term of this patent is extended or adjusted under 35 U.S.C. 154(b) by 662 days.

(21) Appl. No.: 16/587,323

(22) Filed: Sep. 30, 2019

(65) Prior Publication Data

US 2021/0092969 A1   Apr. 1, 2021

(51) Int. Cl.
  *G01N 33/12* (2006.01)
  *A22C 17/00* (2006.01)
  *G01N 23/04* (2018.01)

(52) U.S. Cl.
  CPC ........... *A22C 17/008* (2013.01); *G01N 23/04* (2013.01); *G01N 33/12* (2013.01); *G01N 2223/618* (2013.01); *G01N 2223/643* (2013.01)

(58) Field of Classification Search
  None
  See application file for complete search history.

(56) References Cited

U.S. PATENT DOCUMENTS

| | | | |
|---|---|---|---|
| 5,604,692 A | 2/1997 | Yuyama | |
| 5,745,230 A | 4/1998 | Edwards et al. | |
| 6,546,071 B2 | 4/2003 | Graves | |
| 8,352,068 B2 | 1/2013 | Gudjonsson et al. | |
| 9,159,126 B2 | 10/2015 | Johnson | |
| 10,008,078 B2 | 6/2018 | Kotula | |
| 2002/0012419 A1* | 1/2002 | Graves | A22C 17/008 378/53 |
| 2007/0207242 A1 | 9/2007 | Carlsen | |
| 2009/0130962 A1 | 5/2009 | Willburger et al. | |

(Continued)

FOREIGN PATENT DOCUMENTS

| | | |
|---|---|---|
| EP | 1781110 B1 | 2/2010 |
| EP | 1690144 B1 | 6/2011 |
| WO | 2018087390 A1 | 5/2018 |

OTHER PUBLICATIONS

International Preliminary Report on Patentability (Forms PCT/IPEA/416 and PCT/IPEA/409) dated Dec. 17, 2021, by the International Preliminary Examining Authority, in corresponding International Application No. PCT/US2020/053194. (11 pages).

(Continued)

*Primary Examiner* — Hoon K Song

(74) *Attorney, Agent, or Firm* — Buchanan Ingersoll & Rooney PC

(57) ABSTRACT

Disclosed is a conveyor system including a first conveyor leading to an inspection point, the first conveyor including a diversion mechanism configured to divert an object based on failing to meet an inspection parameter. The system includes a second conveyor configured to transport a container configured to receive the object from the diversion mechanism. A control module is configured to co-register an image of the object captured at the inspection point with container ID data of the container.

20 Claims, 3 Drawing Sheets

(56) References Cited

U.S. PATENT DOCUMENTS

| | | |
|---|---|---|
| 2011/0166696 A1* | 7/2011 | Nignon .................... B07C 5/38 |
| | | 700/223 |
| 2011/0253603 A1 | 10/2011 | Van De Loo |
| 2012/0114103 A1 | 5/2012 | Aust et al. |
| 2018/0314866 A1 | 11/2018 | Kotula |

OTHER PUBLICATIONS

Notification of Transmittal of Supplementary International Search Report or Declaration dated Dec. 23, 2021, by the European Patent Office in corresponding International Application No. PCT/US2020/053194. (12 pages).

International Search Report and Written Opinion of the International Searching Authority (Forms PCT/ISA/220, PCT/SA/210 and PCT/ISA/237) dated Feb. 25, 2021, by the International Bureau of U.S. Patent and Trademark Office in corresponding International Application No. PCT/US 20/53194. (15 pages).

\* cited by examiner

X-RAY INSPECTION OF MEAT

FIELD

Embodiments can relate to a conveyor system including a first conveyor leading to an inspection point, a second conveyor configured to transport a container configured to receive an object from the diversion mechanism, and a control module configured to co-register an image of the object captured at the inspection point with container ID data of the container.

BACKGROUND INFORMATION

Conveyor and inspection systems typically require identification or tracking of rejected items. For instance, when a product being inspected is of such value that simply discarding/throwing it away due to it failing to satisfy an inspection or quality assurance parameter is too expensive, then identification or tracking of the rejected product in the conveyance system would be required. Some products can be packaged into cartons, for example, where the carton can have a barcode prior to entering the inspection point so that when the inspection occurs that carton (and the product therein) can be identified and tracked via the barcode. Yet, sometimes it is not feasible or practical to package the product while in the inspection phase.

For instance, when inspecting bulk meat, it is not feasible or practical to package the meat in a carton before undergoing inspection. Thus, identification information about individual items or chunk of products (CoP, i.e. rejected meat portions) is missing. Know methods for addressing this problem are limited to sequencing the product flow by transporting the product onto a dedicated, controlled conveyor having several sections to facilitate the sequential ordering of inspection. A disadvantage of this approach is that if the product is taken out of the sequencing line, the ability to track the product fails. Inserting a time-dependency can help, but the overall approach is not fail-safe. Additionally, it is difficult to facilitate performing work in parallel at the rework stations due to the requisite that the product being inspected must follow a sequence flow.

Known conveyor and inspection systems can be appreciated from U.S. Pat. No. 6,546,071, U.S. 2009/130962, U.S. 2012/114103, EP 1690144, EP 1781110, and WO 18087390.

SUMMARY

Embodiments of a conveyor system can include a first conveyor leading to an inspection point, the first conveyor including a diversion mechanism configured to divert an object based on failing to meet an inspection parameter and/or a quality assurance parameter. The conveyor system can include a second conveyor configured to transport a container configured to receive the object from the diversion mechanism. The conveyor system can include a control module configured to co-register an image of the object captured at the inspection point with container ID data of the container.

Embodiments of an inspection communication system can include an inspection unit configured to determine whether an object meets an inspection parameter and/or a quality assurance parameter and configured to capture an image of the object. The inspection communication system can include a diversion mechanism configured to divert the object based on failing to meet the inspection parameter. The inspection communication system can include a database configured to receive the image and to receive container ID data of a container. The inspection communication system can include a control module configured to co-register the image with the container ID data. The inspection communication system can include a display configured display the image upon receiving the co-registered image and container ID data.

Embodiments of a method of inspection can involve determining whether an object meets an inspection parameter and/or a quality assurance parameter and capturing an image of the object; diverting the object based on failing to meet the inspection parameter and/or quality assurance parameter; receiving the image and container ID data of a container; co-registering the image with the container ID data; and displaying the image associated with the co-registered image and container ID data.

BRIEF DESCRIPTION OF THE DRAWINGS

Other features and advantages of the present disclosure will become more apparent upon reading the following detailed description in conjunction with the accompanying drawings, wherein like elements are designated by like numerals, and wherein.

DETAILED DESCRIPTION

Figure 1:
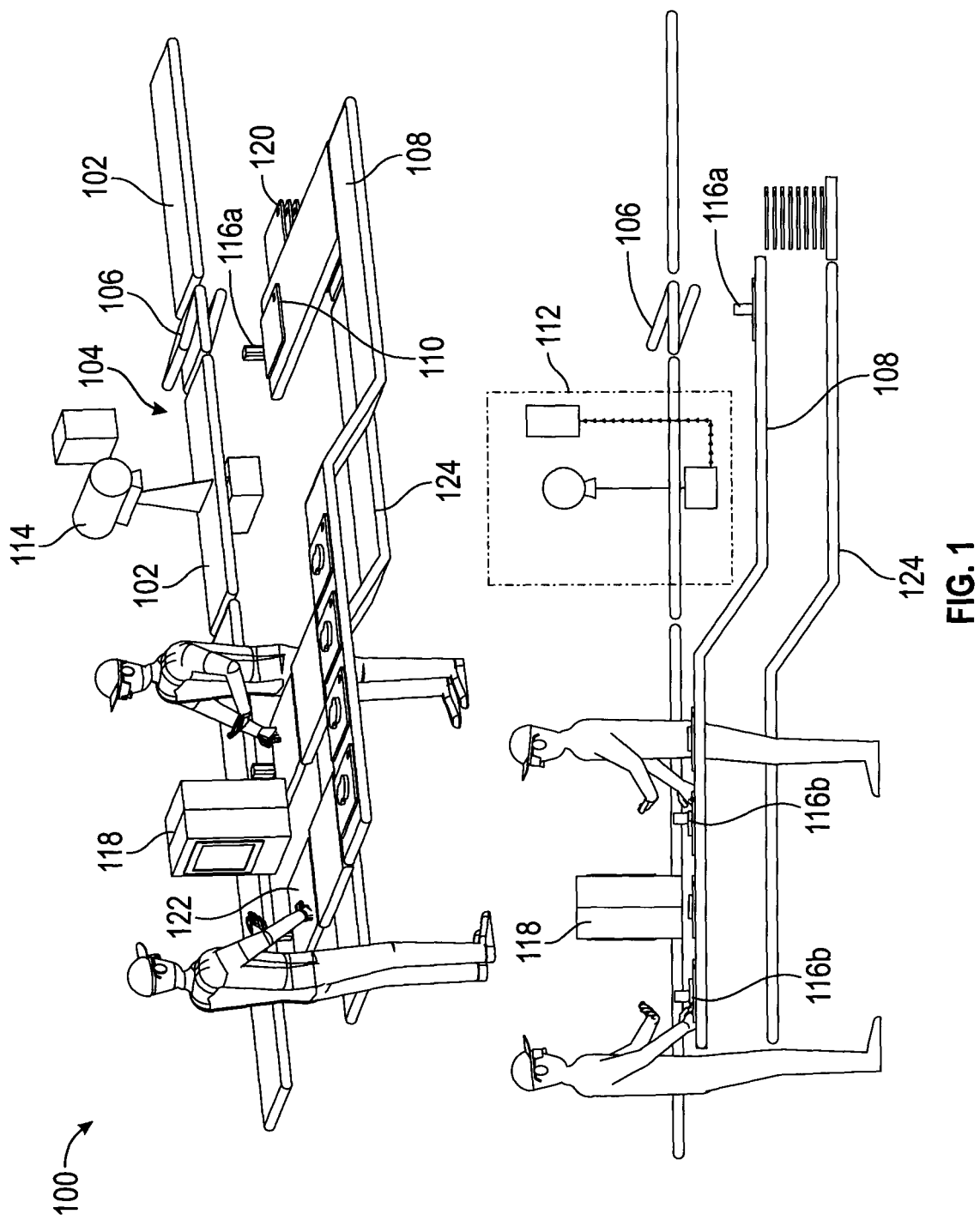
FIG. 1 shows an exemplary conveyor system that may be used for embodiments of an inspection system.

Referring to FIG. 1, embodiments of the conveyor system 100 can include a first conveyor 102 leading to an inspection point 104, the first conveyor 102 including a diversion mechanism 106 configured to divert an object based on failing to meet an inspection parameter. The conveyor system 100 can include a second conveyor 108 configured to transport a container 110 (e.g., a tray, a bin, a crate, etc.) configured to receive the object from the diversion mechanism 106. The conveyor system 100 is contemplated to be a belt-fed system, but it can be a screw-feed system, bucket-fed system, airflow system, etc. With the conveyor system 100 designed as a belt-fed system, other components such as belts, rollers, drivers, motors, etc. can be included for the proper operation of such a conveyance system. The configuration, inter relation, and operation of such components are well known.

The conveyor system 100 can include a control module 112 that controls various aspects of the conveyor system 100 and inspection communication system 200. The control module 112 can be a processor in operative association with a memory. In some embodiments, the control module 112 can be configured to co-register an image of the object captured at the inspection point 104 with container ID data of the container 110.

In an exemplary embodiment, the conveyor system 100 includes a first conveyor 102 leading to an inspection point 104, the first conveyor 102 transporting an object to the inspection point 104. The inspection point 104 can have an inspection unit 114 configured to determine if the object traveling through the inspection point 104 meets or fails to meet the inspection parameter. The determination of whether the object traveling through the inspection point meets or fails to meet the inspection parameter is sent to the control module 112. If the control module 112 receives information that the object meets the inspection parameter, the object continues along the first conveyor 102. This can include being transported past the inspection point 104 and following the first conveyor 102 for further processing. If the control module 112 receives information that the object fails to meet the inspection parameter, the control module 112 activates the diversion mechanism 106 to cause the object to divert from the path of the first conveyor 102. This can include being transported past the inspection point 104 and following the first conveyor 102 to the diversion mechanism 106 where the object is then diverted to the second conveyor 108. In addition, when the control module 112 receives information that the object fails to meet the inspection parameter, the control module 112 causes the inspection unit 114 to capture an image of the object while the object is at the inspection point 104. The control module 112 receives the image of the object from the inspection unit 114 and generates an image identifier. The control module 112 can convert the image and image identifier into digital data. In some embodiments, this digital data is transmitted to a database 202 (see FIG. 2) for storage and later retrieval.

The diversion mechanism 106 can be a mechanical switch (e.g., a flap sorting switch) in operative communication with the control module 112 that, when activated, causes the object to follow an alternative route. For instance, the first conveyor 102 can comprise segments of conveyor belts, at least one of which is pivotally attached so as to allow it to swing like a flap. When all the segments are in alignment (e.g., the flapping segment is not actuated), the object flows over the segments in a contiguous manner. When the flapping segment is actuated, it rotates (e.g. downward) to allow the object to be directed downward and fall through to the second conveyor 108 that is located underneath the segmented first conveyor 102. When the an object fails to meet an inspection parameter, the control module 112 can control the diversion mechanism 106 and cause the object to be removed from the first conveyor path, diverting the object to the second conveyor 108.

It should be noted that additional objects can be transported through the inspection point 104 for inspection as the object that failed to meet the inspection parameter is diverted to the second conveyor 108. Thus, the operation can persist on a continuous flow basis. Any object that meets the inspection parameter continues on the path of the first conveyor 102, and any object that fails to meet the inspection parameter is imaged and is diverted to follow the path of the second conveyor 108 while the image taken of that object is transmitted to the database 202. The objects failing to meet the inspection parameter flow out from the path of the first conveyor 102 in sequential order and are thus diverted in sequential order. The images of them can be stored in sequential order in the database 202. When the object is diverted, it is caused to fall into or onto a container 110 that is being transported by the second conveyor 108. Each container 110 has a mark 120 with container ID data. The container ID data is obtained from a first reader 116a scanning the mark 120, and this container ID data is transmitted to the control module 112 and/or database 202. The control module 112 retrieves the image identifier associated with the object that had been diverted to the container 110 and co-registers the image of the object with the container ID data. The second conveyor 108 then transports the container 110 with the object to a rework station 122.

Once at the rework station 122, a user can input the container ID data via a user interface displayed on a display 118 or the system automatically detects the container 110 via the container ID data (e.g., a second reader 116b associated with the display 118 can be used to retrieve the container ID data). The display 118 and/or second reader 116b transmits the container ID data to the control module 112. The control module 112 retrieves the co-registered image of the object associated with that container ID data from the database 202 and transmits the co-registered image 204 (see FIG. 2) to the display 118. The display 118 displays the image of the object. A user can then view the image of the object via the display 118 to assist the user in reworking the object (e.g., making corrections to the object so that it can meet the inspection parameter). The reworked object can be placed back onto the first conveyor 102 to be transported through the inspection point for another inspection. Placing the reworked object can include physically placing the object by a user or by another conveyor transporting the object to the first conveyor 102 at a point before the inspection point 104.

As noted above, the conveyor system 100 can include an inspection unit 114 configured to determine whether the object meets the inspection parameter. The inspection unit 114 can include any one or combination of an optical camera, x-ray unit, infrared unit, ultraviolet light unit, microwave unit, ultrasound unit, spectroscopy unit, etc. The inspection unit 114 can include an image capturing device configured to receive electromagnetic radiation (EMR) or ultrasound waves (US) and analyze the EMR or US based on the wavelength, amplitude, phase, polarization, etc. For instance, the image capturing device can include circuitry (e.g., processor, filter circuits, transducer, sensors, etc.) and a power supply 206 to receive EMR or US, process it, and generate an output that is an image representation of the EMR or US.

As noted above, the conveyor system 100 can include a mark 120 attached to the container 110, the mark 120 being configured to contain the container ID data. The mark 120 can include any one or combination of a radio frequency identification tag, a barcode, a Quick Response code, an infrared identifying marking, an ultraviolet identifying marking, a color marking identifiable by optical camera, etc.

As noted above, the conveyor system 100 can include a first reader 116a and/or a second reader 116b, each configured to receive container ID data by scanning the mark 120. The reader(s) 116a, 116b can be a RFID scanner, a laser scanner, etc. The first reader 116a can be located at the container queue (the line by which the container 110 is held to await its turn to be paced on the second conveyor 108 when prompted to do so). The second reader 116b can be located at or near the display 118.

As noted above, the second conveyor 108 can be configured to transport the object and the container 110 to a rework station 122. The conveyor system 100 can include a display 118 located at the rework station 122, the display being configured to receive the co-registered image and container ID data 204, and display the image of the object associated with the container 110 at the rework station 122.

The display 118 can be a computer monitor in connection with a computer device, for example. The display 118 can be programmed to operate a reject classification engine that is configured to allow a user to indicate (via the user interface) whether their inspection of the object at the rework station 122 also results in a failure to meet the inspection parameter. In other words, the user at the rework station 122 can verify whether the object was validly rejected. This can be done to assist with process quality control of the system 100. For instance, if the inspection unit 114 is rejecting objects for failing to meet the inspection parameter but upon subsequent inspection by a user it is discovered that the object does in fact meet the inspection parameter, then these instances can be recorded by a user entering their observations via the user interface associated with the reject classification engine. In addition, the reject classification engine can allow users to add textual inputs regarding their observations. For instance, if the inspection parameter includes the presence of a bone as a contaminant in meat, then a user can input textual information about the contaminants they observe when the rejected meat reaches their rework station 122. The user can indicate whether the contaminant is actually bone or some other contaminant (e.g., white colored plastic), or whether they observe contaminant in addition to bone that the system 100 failed to identify, etc.

Data from the reject classification engine can be transmitted to the database 202 for storage and later retrieval. This data can be time stamped, embedded with metadata, include the image identifier and/or container ID data, etc. to assist with recording and categorizing information about each individual rejected object. The display 118 can generate reports regarding statistics of the rejects and the user-classifications of them by acquisitioning the stored data from the database 202. In some embodiments, reports can be generated to assist with quality assurance and process quality of the system 100. In some embodiments, reports can be generated to be shared with vendors of the objects so as to inform the vendors that the objects being supplied are not meeting certain quality specifications, and to assist the vendors in identifying the problem by providing them with details of the rejected objects.

The conveyor system 100 can include a third conveyor 124 configured to transport the container 110 to the second conveyor 108 at the diversion mechanism 106, and transport the container 110 away from the second conveyor 108 at the rework station 122. For instance, the conveyor system 100 can include a first conveyor 102 leading to an inspection point 104, the first conveyor 102 transporting an object to the inspection point 104. The inspection point 104 can have an inspection unit 114 configured to determine if the object traveling through the inspection point 104 meets or fails to meet the inspection parameter. If the control module 112 receives information that the object meets the inspection parameter, the object continues along the first conveyor 102. If the control module 112 receives information that the object fails to meet the inspection parameter, the control module 112 activates the diversion mechanism 106 to cause the object to divert from the path of the first conveyor 102. This can include being transported past the inspection point 104 and following the first conveyor 102 to the diversion mechanism 106 where the object is then diverted to the second conveyor 108. The object being diverted to the second conveyor 108 can fall into or on a container 110. The second conveyor 108 then transports the container 110 with the object to a rework station 122. After being reworked at the rework station 122, the object is removed from the container 110, wherein the container 110 is caused to follow the third conveyor 124. The third conveyor 124 can transport the container 110 back to the second conveyor 108 at the diversion mechanism 106 to be placed in a queue, the queue being a line by which the container 110 is held to await being placed on the second conveyor 108 when prompted to do so.

It should be noted that other means for returning the container 110 back to the container queue can be used. For instance, a trolley or cart can be used instead of the third conveyor 124.

The object can be meat and the inspection parameter can be determining whether the meat has contaminant that is equal to and/or greater than the predetermined amount. The contaminant can include bone. For instance, the inspection parameter can be an assessment of whether the meat contains any bone, a certain amount of bone, a certain size of bone, a certain bone-to-meat ratio, etc.

In some embodiments, the conveyor system 100 includes the object.

While it is contemplated for the conveyor system 100 and inspection unit 114 to be used to transport and inspect meat as the object, the conveyor system 100 and inspection unit 114 can be used for any type of object that is to be transported via a conveyor. It should be further noted that the inspection parameter can be any quantitative or qualitative measure, including a quality assurance parameter. For instance, the inspection parameter can be a measure of contaminant in or on the object, mis- or deformation of the object, missing or incomplete component for the object, undesired composition or chemistry of the object, incorrect count for components forming the object, incorrect weight of the object, incorrect color of the object, incorrect position of the object, etc.

The conveyor system 100 can be used to convey and inspect objects in a way to allow for defective objects to be diverted from the acceptable object flow path (first conveyor path) and be reworked at a rework station 122 in a rejected object flow path (second conveyor path) without having the interrupt the acceptable object flow, while still keeping track of the defective objects, and also allowing for re-introduction of the reworked object back into the conveyor system 100 for additional inspection. The conveyor system 100 can also be used to facilitate parallel inspection operations (e.g., deviate from the strict sequential flow required by known inspection systems). For instance, the conveyor system 100 can adequately track objects that are diverted to the second conveyor path, provides an image of that object to assist users in reworking the object, and tracks when the object is placed back into the inspection process. The conveyor system 100 also provides the means to have multiple second conveyors 108 and/or third conveyors 124 in operation so that multiple rework stations 122 can be operated simultaneously. This type of operational flexibility is not possible with known systems. The ability to perform such operations can be attributed to the conveyor system 100 configuration described herein, as well as the information data flow. The information data flow can be achieved with the inspection communication system 200 that will be described next.

Figure 2:
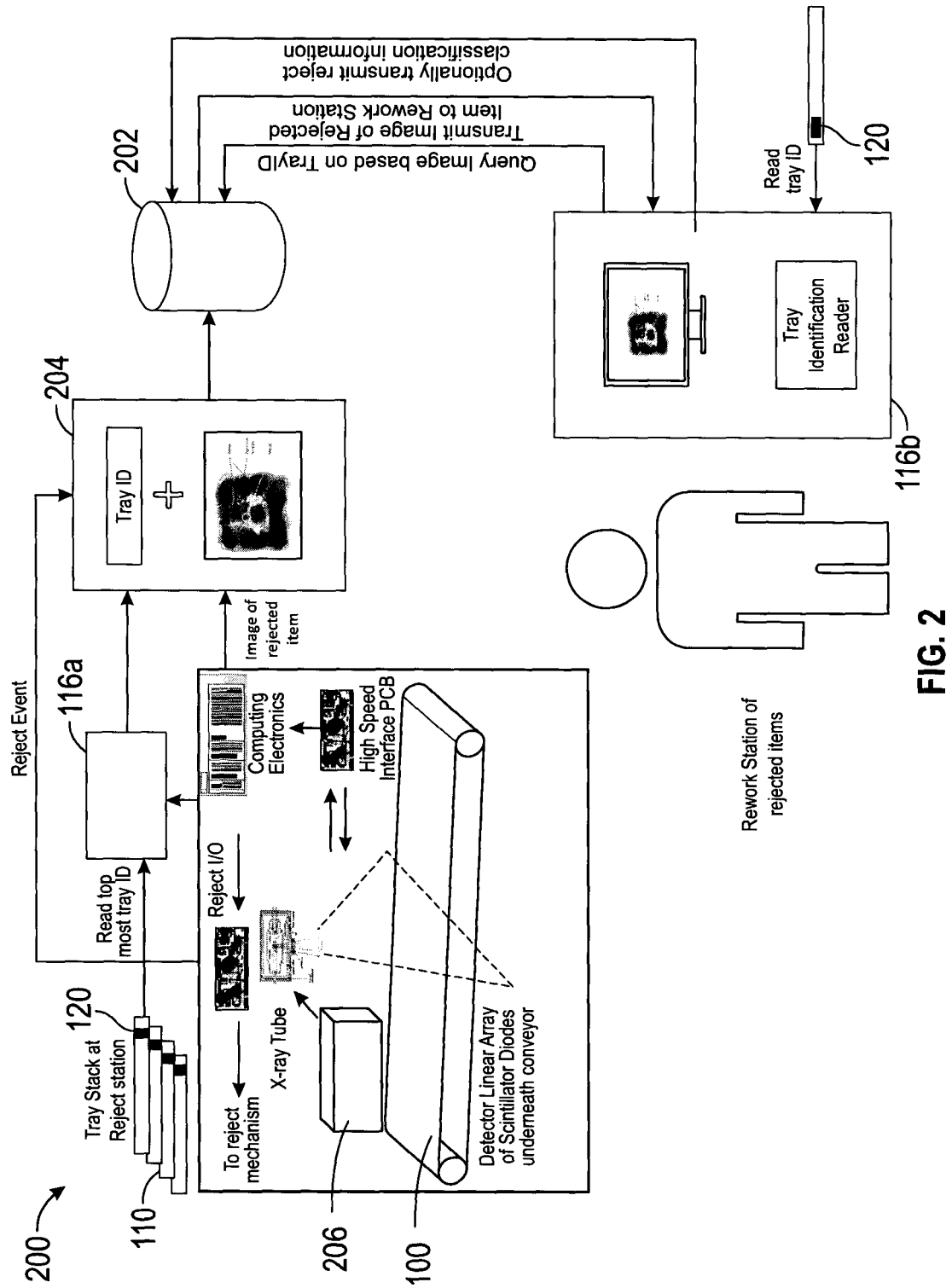
FIG. 2 shows an exemplary data flow diagram that may be used for embodiments of an inspection system.
Figure 3:
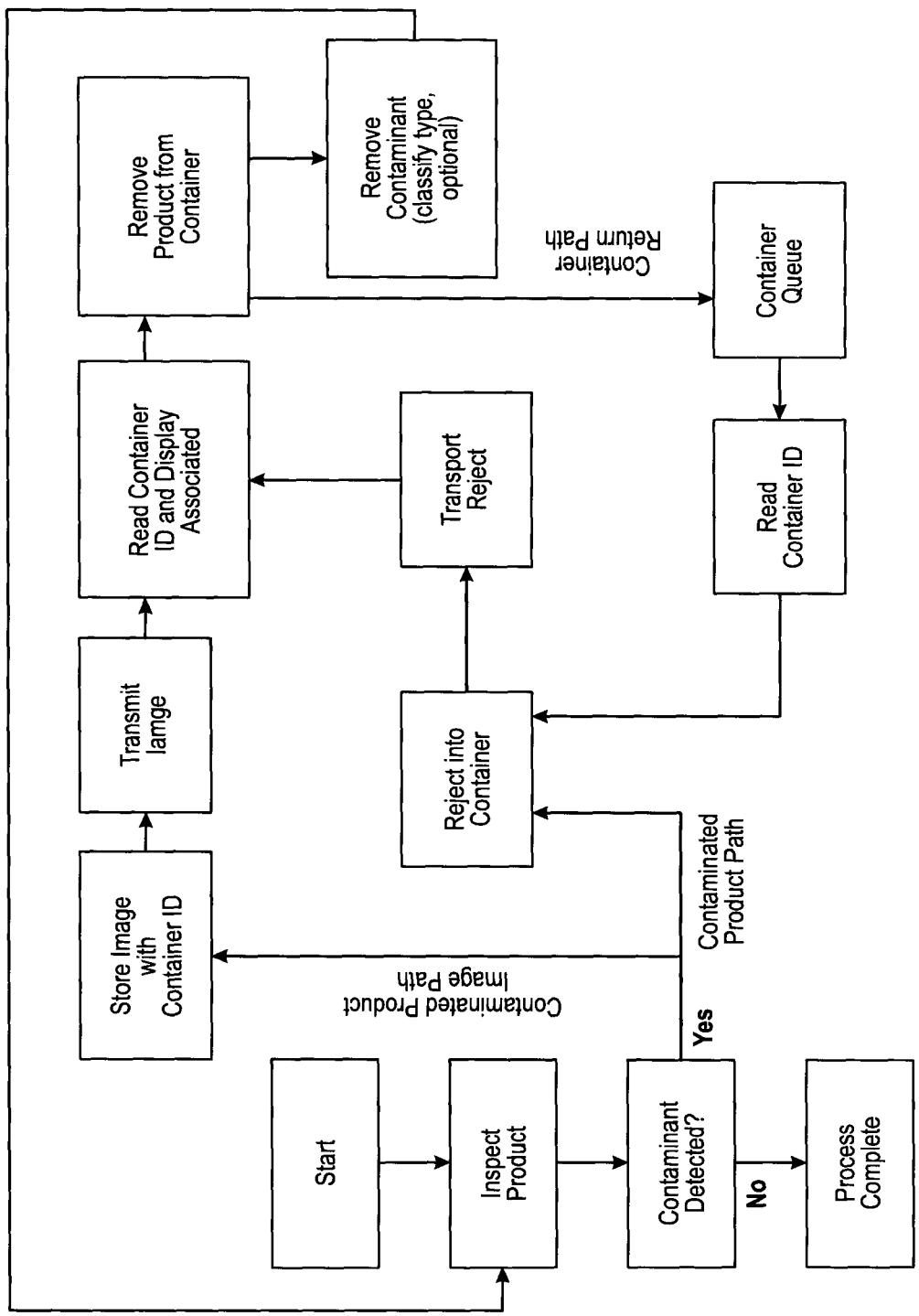
FIG. 3 shows an exemplary process flow diagram that may be used for embodiments of an inspection system.

Referring to FIGS. 2 and 3, some embodiments of the conveyor system 100 (or aspects thereof) can be configured to be part of or used in conjunction with an inspection communication system 200. For instance, the inspection communication system 200 can include the inspection unit 114 configured to determine whether an object meets an inspection parameter and configured to capture an image of the object. The inspection communication system 200 can also include the diversion mechanism 106 (see FIG. 1) configured to divert the object based on failing to meet the inspection parameter. The inspection communication system 200 can also include the database 202 configured to receive the image and to receive container ID data 120 of a container 110. The inspection communication system 200 can also include the control module 112 configured to co-register the image with the container ID data. The inspection communication system 200 can also include the display 118 configured display the image upon receiving the co-registered image and container ID data 204.

The inspection unit 114 can include any one or combination of an optical camera, x-ray unit, infrared unit, ultraviolet light unit, microwave unit, ultrasound unit, spectroscopy unit, etc.

The inspection communication system 200 can include the mark 120 attached to the container, the mark 120 being configured to contain the container ID data. The mark 120 can include any one or combination of a radio frequency identification tag, a barcode, a Quick Response code, an infrared identifying marking, an ultraviolet identifying marking, a color marking identifiable by optical camera, etc.

The inspection communication system 200 can include the reader 116 configured to receive the container ID data and transmit the container ID data to the database 202.

Various components of the conveyor system 100 and inspection communication system 200 (e.g., the control module 112, the reader 116, the display 118, the inspection unit 114, etc.) can include a processor in operative association with a memory. Any of the processors disclosed herein can be at least a one of a scalable processor, a parallelizable processor, etc. Any of the processors can be optimized for multi-thread processing capabilities. In some embodiments, the processor can be a graphics processing unit (GPU). The processor can include any integrated circuit or other electronic device (or collection of devices) capable of performing an operation on at least one instruction, which can be any one or combination of a Reduced Instruction Set Core (RISC) processor, a CISC microprocessor, a Microcontroller Unit (MCU), a CISC-based Central Processing Unit (CPU), a Digital Signal Processor (DSP), etc. The hardware of such devices may be integrated onto a single substrate (e.g., silicon "die"), or distributed among two or more substrates. Various functional aspects of the processor may be implemented solely as software or firmware associated with the processor.

The memory can include computer program code stored thereon. The memory can be optionally associated with a processor. Embodiments of the memory can include a volatile memory store (such as RAM), non-volatile memory store (such as ROM, flash memory, etc.) or some combination of the two. For instance, the memory can include, but is not limited to, RAM, ROM, EEPROM, flash memory, CDROM, digital versatile disk (DVD) or other optical storage, magnetic cassette, magnetic tape, magnetic disk storage or other magnetic storage device, or any other medium which can be used to store the desired information and that can accessed by the processor. The memory can be a non-transitory computer-readable medium. The term "computer-readable medium" (or "machine-readable medium") as used herein is an extensible term that refers to any medium or any memory that participates in providing instructions to a processor for execution, or any mechanism for storing or transmitting information in a form readable by a machine (e.g., a computer). Such a medium may store computer-executable instructions to be executed by a processing element, control logic, and/or data which are manipulated by a processing element and/or control logic, the medium being able to take many forms, including but not limited to, non-volatile medium, volatile medium, and transmission media.

Transmission media can include coaxial cables, copper wire and fiber optics, which can include the wires that include or form a bus. Transmission media can also take the form of acoustic or light waves, such as those generated during radio-wave and infrared data communications, or other form of propagated signals (e.g., carrier waves, infrared signals, digital signals, etc.). Forms of computer-readable media include, for example, a floppy disk, a flexible disk, hard disk, magnetic tape, or any other magnetic medium, a CD-ROM, any other optical medium, punchcards, paper-tape, any other physical medium with patterns of holes, a RAM, a PROM, and EPROM, a FLASH-EPROM, any other memory chip or cartridge, a carrier wave as described hereinafter, or any other medium from which a computer can read.

Instructions for implementation of any of the methods disclosed herein can be stored on the memory in the form of computer program code. The computer program code can include program logic, control logic, or other algorithms that may or may not be based on artificial intelligence (e.g., machine learning techniques, artificial neural network techniques, etc.). The memory and the computer program code can be configured to cause the processor associated therewith to implement any of the methods disclosed herein.

Any of the components of the conveyor system 100 and inspection communication system 200 can include a communication interface (e.g., hardwire connection, transceiver, gateway, etc.) to facilitate transmitting and receiving communication signals. As noted above, the control module 112 can be configured to control various aspects of the conveyor system 100 and inspection communication system 200. For instance, the control module 112 can be configured to control the inspection unit 114, the diversion mechanism 106, the reader 116, and the display 118. The control module 112 can also access the database 202. Thus, the control module 112 can include a communication interface to facilitate transmitting and receiving communication signals to and from the inspection unit 114, the diversion mechanism 106, the reader 116, the display 118, and the database 202.

A method of inspection can involve determining whether an object meets an inspection parameter and/or a quality assurance parameter and capturing an image of the object. The method of inspection can involve diverting the object based on failing to meet the inspection parameter quality assurance parameter. The method of inspection can involve receiving the image and container ID data of the container 110. The method of inspection can involve co-registering the image with the container ID data. The method of inspection can involve displaying the image associated with the co-registered image and container ID data 204.

Displaying the image can occur at a rework station 122, and the method can further involve reworking the object to remove a contaminant.

The method of inspection can involve reworking the object and determining whether the reworked object meets the inspection parameter and/or the quality assurance parameter.

In an exemplary implementation, a first object is transported along the first conveyor 102 to the inspection point 104 where it is inspected by the inspection unit 114. The inspection unit 114 determines if the first object meets the inspection parameter and/or the quality assurance parameter. Assuming the first object meets the inspection parameter and/or the quality assurance parameter, the first object continues along the first conveyor 102, passes over the diversion mechanism 106 and onto further processing. A second object is transported along the first conveyor 102 to the inspection point 104. The inspection unit 114 determines if the second object meets the inspection parameter and/or the quality assurance parameter. Assuming the second object fails to meet the inspection parameter and/or the quality assurance parameter, the inspection unit captures an image of the second object and transmits the image and the failure to meet information to the control module 112. The control module 112 generates an image identifier and transmits digital data representing the image and image identifier to the database 202 for storage and later retrieval. The control module 112 sends a signal to the diversion mechanism 106 to cause the second object to be diverted to the second conveyor 108 after the second object continues past the inspection point 104. While the second object is being diverted to the second conveyor 108, a third object is transported along the first conveyor 102 to the inspection point 104. The inspection unit 114 determines if the third object meets the inspection parameter and/or the quality assurance parameter. Assuming the third object meets the inspection parameter and/or the quality assurance parameter, the third object continues along the first conveyor 102, passes over the diversion mechanism 106 and onto further processing. A fourth object is transported along the first conveyor 102 to the inspection point 104. The inspection unit 114 determines if the fourth object meets the inspection parameter and/or the quality assurance parameter. Assuming the fourth object fails to meet the inspection parameter and/or the quality assurance parameter, the inspection unit 114 captures an image of the fourth object and transmits the image and the failure to meet information to the control module 112. The control module 112 generates an image identifier and transmits digital data representing the image and image identifier to the database 202 for storage and later retrieval. The control module 112 sends a signal to the diversion mechanism 106 to cause the fourth object to be diverted to the second conveyor 108 after the fourth object continues past the inspection point 104.

When diverted to the second conveyor 108, the second object falls into or onto a first container 110 (having a mark 120 with a first container ID data). The reader 116 reads the mark 120 to acquisition the first container ID data and transmits it to the control module 112. The control module 112 retrieves the image identifier associated with the second object that had been diverted to the first container 110 and co-registers the image of the second object with the first container ID data. The second conveyor 108 then transports the first container 110 with the second object to the rework station 122, where the second reader 116*b* at or near the display 118 is located. Once at the rework station 122, the system automatically detects the first container 110 via the first container ID data (e.g., a second reader 116 at the display 118 reading the mark 120). The display 118 transmits the first container ID data to the control module 112. The control module 112 retrieves the co-registered image 204 of the second object and causes the display 118 to display the image of the second object. A user can then view the image of the second object displayed on the display 118 to assist the user in reworking the second object (e.g., making corrections to the object so that it can meet the inspection parameter and/or quality assurance parameter). The reworked second object can be placed the back onto the first conveyor 102 to be transported through the inspection point for another inspection. The first container 110 can be placed on the third conveyor 124 at the rework station 122 to be transported back to the queue adjacent the diversion mechanism 106.

When diverted to the second conveyor 108, the fourth object falls into or onto a second container 110 (having a mark 120 with second container ID data). The reader 116 reads the mark 120 to acquisition the second container ID data and transmits it to the control module 112. The control module 112 retrieves the image identifier associated with the fourth object that had been diverted to the second container 110 and co-registers the image of the fourth object with the second container ID data. The second conveyor 108 then transports the second container 110 with the fourth object to the rework station 122, where the display 118 is located. Once at the rework station 122, the system automatically detects the second container 110 via the second container ID data (e.g., a second reader 116 at the display 118 reading the mark 120). The display 118 and/or second reader 116*b* transmits the second container ID data to the control module 112. The control module 112 retrieves the co-registered image 204 of the fourth object and causes the display 118 to display the image of the fourth object. A user can then view the image of the fourth object to assist the user in reworking the fourth object (e.g., making corrections to the object so that it can meet the inspection parameter and/or quality assurance parameter). The reworked fourth object can be placed the back onto the first conveyor 102 to be transported through the inspection point for another inspection. The second container 110 can be placed on the third conveyor 124 at the rework station 122 to be transported back to the queue adjacent the diversion mechanism 106.

It will be understood that modifications to the embodiments disclosed herein can be made to meet a particular set of design criteria. For instance, any component or process step can be any suitable number or type of each to meet a particular objective. Therefore, while certain exemplary embodiments of the system and method of using and making the same have been discussed and illustrated, it is to be distinctly understood that the invention is not limited thereto but can be otherwise variously embodied and practiced within the scope of the following claims.

It will be appreciated that some components, features, and/or configurations can be described in connection with only one particular embodiment, but these same components, features, and/or configurations can be applied or used with many other embodiments and should be considered applicable to the other embodiments, unless stated otherwise or unless such a component, feature, and/or configuration is technically impossible to use with the other embodiment. Thus, the components, features, and/or configurations of the various embodiments can be combined together in any manner and such combinations are expressly contemplated and disclosed by this statement.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein. Additionally, the disclosure of a range of values is a disclosure of every numerical value within that range, including the end points.

What is claimed is:

1. A conveyor system, comprising:
   a first conveyor leading to an inspection point, the first conveyor including a diversion mechanism configured to divert an object based on failing to meet an inspection parameter and/or quality assurance parameter;
   a second conveyor configured to transport an empty container configured to receive the object from the diversion mechanism and transport the container having the object to a rework station;
   a third conveyor configured to transport the empty container away from the second conveyor at the rework station and deliver the empty container to the second conveyor at the diversion mechanism; and
   a control module configured to co-register an image of the object captured at the inspection point with container ID data of the container.

2. The conveyor system recited in claim 1, comprising:
an inspection unit configured to determine whether the object meets the inspection parameter and/or quality assurance parameter.

3. The conveyor system recited in claim 2, wherein the inspection unit includes any one or combination of an optical camera, x-ray unit, infrared unit, ultraviolet light unit, microwave unit, ultrasound unit, or spectroscopy unit.

4. The conveyor system recited in claim 1, comprising:
a mark attached to the container, the mark configured to contain the container ID data.

5. The conveyor system recited in claim 4, wherein the mark includes any one or combination of a radio frequency identification tag, a barcode, a Quick Response code, an infrared identifying marking, an ultraviolet identifying marking, or a color marking identifiable by optical camera.

6. The conveyor system recited in claim 4, comprising:
a reader configured to receive container ID data.

7. The conveyor system recited in claim 1, comprising:
a display configured to receive the co-registered image and container ID data, and display the image of the object associated with the container at the rework station.

8. The conveyor system recited in claim 1, wherein the object is meat and the inspection parameter and/or quality assurance parameter is determining whether the meat has contaminant that is equal to and/or greater than the predetermined amount.

9. The conveyor system recited in claim 8, wherein the contaminant includes bone.

10. The conveyor system recited in claim 1, in combination with the object.

11. An inspection communication system, comprising:
a conveying system including a first conveyor, a second conveyor, and a third conveyor;
an inspection unit configured to determine whether an object traveling on the first conveyor meets an inspection parameter and/or quality assurance parameter and configured to capture an image of the object;
a diversion mechanism configured to divert the object based on failing to meet the inspection parameter, wherein:
the diversion mechanism is configured to divert the object to an empty container located on the second conveyor, wherein the second conveyor is configured to transport the container having the object to a rework station; and
the third conveyor is configured to transport the empty container from the second conveyor at the rework station and back to the second conveyor at the diversion mechanism;
a database configured to receive the image and to receive container ID data of a container;
a control module configured to co-register the image with the container ID data; and
a display configured display the image upon receiving the co-registered image and container ID data.

12. The inspection communication system recited in claim 11, wherein the inspection unit includes any one or combination of an optical camera, x-ray unit, infrared unit, ultraviolet light unit, microwave unit, ultrasound unit, or spectroscopy unit.

13. The inspection communication system recited in claim 11, comprising: a mark attached to the container, the mark configured to contain the container ID data.

14. The inspection communication system recited in claim 13, wherein the mark includes any one or combination of a radio frequency identification tag, a barcode, a Quick Response code, an infrared identifying marking, an ultraviolet identifying marking, or a color marking identifiable by optical camera.

15. The inspection communication system recited in claim 11, comprising:
a reader configured to receive the container ID data and transmit the container ID data to the database.

16. A method of inspection, the method comprising:
determining whether an object meets an inspection parameter and/or a quality assurance parameter and capturing an image of the object;
diverting the object based on failing to meet the inspection parameter and/or quality assurance parameter such that:
the object is diverted from a first conveyor to an empty container located on a second conveyor;
the second conveyor transports the container having the object to a rework station; and
a third conveyor transports the empty container away from the second conveyor at the rework station and delivers the empty container to the second conveyor at the diversion point;
receiving the image and container ID data of a container;
co-registering the image with the container ID data; and
displaying the image associated with the co-registered image and container ID data.

17. The method recited in claim 16, wherein displaying the image occurs at a rework station, the method comprising:
reworking the object to remove a contaminant.

18. The method recited in claim 16, comprising:
reworking the object and determining whether the reworked object meets the inspection parameter and/or the quality assurance parameter.

19. The conveyor system recited in claim 7, wherein the display is programmed to operate a reject classification engine configured to allow a user to indicate whether an inspection of the object at the rework station also results in the failure to meet the inspection parameter and/or quality assurance parameter.

20. The conveyor system recited in claim 19, wherein the reject classification engine is configured to cause the display to generate a report regarding statistics of objects inspected at the rework station.

* * * * *